(12) United States Patent
Bjorndal et al.

(10) Patent No.: US 7,704,731 B2
(45) Date of Patent: Apr. 27, 2010

(54) SYSTEM AND METHOD FOR QUANTIFYING TOXICITY IN WATER, SOIL, AND SEDIMENTS

(75) Inventors: Bryan Bjorndal, Carlsbad, CA (US); David Lapota, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 869 days.

(21) Appl. No.: 11/586,745

(22) Filed: Oct. 10, 2006

(65) Prior Publication Data
US 2008/0085504 A1    Apr. 10, 2008

(51) Int. Cl.
C12M 1/34 (2006.01)
C12M 1/36 (2006.01)
C12M 1/38 (2006.01)
C12M 3/00 (2006.01)

(52) U.S. Cl. .............................. 435/288.7; 435/286.7
(58) Field of Classification Search .............. 435/286.7, 435/88.72
See application file for complete search history.

(56) References Cited

U.S. PATENT DOCUMENTS

| | | | |
|---|---|---|---|
| 4,978,854 A | 12/1990 | Lapota et al. | |
| 5,225,333 A * | 7/1993 | Krause et al. | 435/32 |
| 5,329,353 A | 7/1994 | Ichimura et al. | |
| 5,441,873 A * | 8/1995 | Knight et al. | 435/34 |
| 5,565,360 A * | 10/1996 | Lapota et al. | 435/286.7 |
| 5,580,785 A | 12/1996 | Stiffey et al. | |
| 5,840,572 A | 11/1998 | Copeland et al. | |
| 6,117,643 A * | 9/2000 | Simpson et al. | 435/7.1 |
| 2006/0014228 A1* | 1/2006 | Simpson et al. | 435/7.32 |

FOREIGN PATENT DOCUMENTS

GB    2005018 A  *  4/1979

OTHER PUBLICATIONS

Cussatlegras et al., (Bioluminescence of the dinoflagellate Pyrocystis noctiluca induced by laminar and turbulent Couette flow. 2004. Journal of Experimental Marine Biology and Ecology, vol. 310, pp. 227-246).*

* cited by examiner

*Primary Examiner*—Walter D Griffin
*Assistant Examiner*—Lydia Edwards
(74) *Attorney, Agent, or Firm*—Kyle Eppele; J. Eric Anderson (57) ABSTRACT

A toxicity test system comprising an aqueous suspension of dinoflagellates; a test chamber capable of containing the aqueous suspension and a test sample; an optical signal generator capable of emitting an excitation signal, which is capable of exciting the dinoflagellates to emit a fluorescence signal if the dinoflagellates are alive; a first optical transducer capable of producing a first data signal in response to detecting to the fluorescence signal; a stimulator capable of generating a pressure pulse, which is capable of stimulating the dinoflagellates to emit a bioluminescence signal if the dinoflagellates are alive; a second optical transducer capable producing a second data signal in response to detecting the bioluminescence signal; and an analyzer disposed to compare the first data signal and the second data signal to a control data to generate an output representative of the toxicity of the test sample.

19 Claims, 9 Drawing Sheets

SYSTEM AND METHOD FOR QUANTIFYING TOXICITY IN WATER, SOIL, AND SEDIMENTS

FEDERALLY-SPONSORED RESEARCH AND DEVELOPMENT

This invention was developed with federal funds and is assigned to the United States Government. Licensing and technical inquiries may be directed to the Office of Patent Counsel, Space and Naval Warfare Systems Center, San Diego, Code 20012, San Diego, Calif., 92152; telephone (619) 553-3001, facsimile (619) 553-3821. Reference Navy Case No. 98125.

CROSS-REFERENCE TO RELATED APPLICATIONS

This application is related to U.S. application Ser. No. 11/586,747, filed Oct. 10, 2006, entitled "Method for Stimulation of Bioluminescent Organisms Via Turbulence Created by Gas Bubbles" (Navy Case #98122).

BACKGROUND OF THE INVENTION

Current systems for quantifying toxicity in water, soil, and sediments tend to be complex, expensive, time consuming, and imprecise. A need exists for an easier to use, less expensive, quicker, and more precise system for quantifying toxicity in soils, sediments, and water.

BRIEF DESCRIPTION OF THE DRAWINGS

Throughout the several views, like elements are referenced using like references. Figures are not drawn to scale.

DETAILED DESCRIPTION OF EMBODIMENTS

Figure 1:
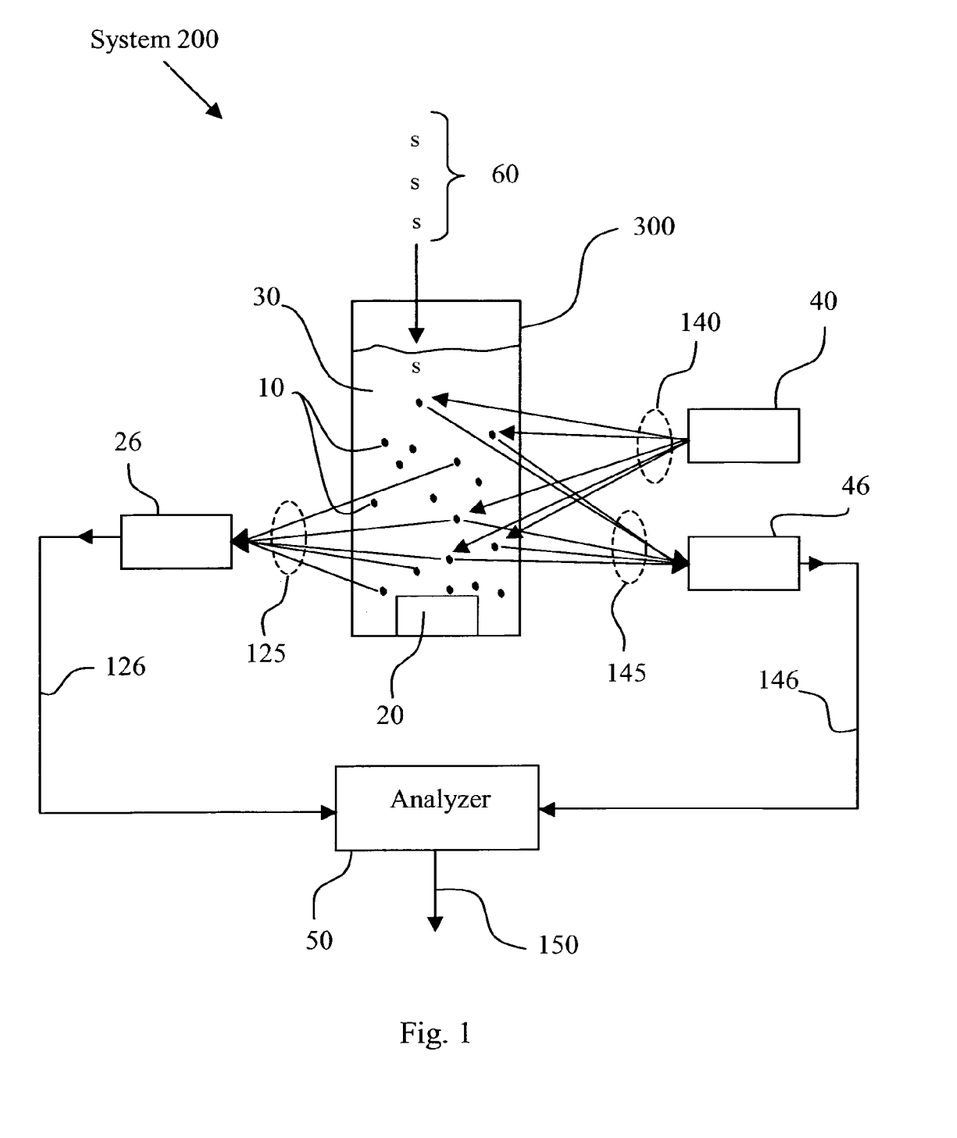
FIG. 1 shows an embodiment of a toxicity test system.

Toxicity test system 200, as shown in FIG. 1, accurately quantifies the toxicity of a test sample 60 by: combining the test sample 60 with an aqueous suspension 30 of dinoflagellates 10; testing both the chlorophyll-a fluorescence and the bioluminescence capabilities of the dinoflagellates 10; and then comparing the bioluminescence and fluorescence test results with control test results. The presence of toxins inhibits the ability of the dinoflagellates 10 to fluoresce and bioluminesce. Thus, exposing some dinoflagellates 10 to test sample 60 and then determining the degree of fluorescence and bioluminescence inhibition in the exposed dinoflagellates 10 provides accurate information as to the health of the dinoflagellates 10, and by extension, the toxicity of the test sample 60. The degree of fluorescence and bioluminescence inhibition in the dinoflagellates 10 due to exposure to the test sample 60 may be determined by comparing the fluorescence and bioluminescence test data of the exposed dinoflagellates 10 to the fluorescence and bioluminescence test data of a control group of dinoflagellates 10. Correlation of the test data from both the fluorescence and bioluminescence tests provide more thorough and accurate information about the toxicity of test sample 60 than data from either bioluminescence or fluorescence testing alone. High correlation of the test data between the bioluminescence and fluorescence tests on the same dinoflagellates 10 provides assurance of test data accuracy. On the other hand, if a large discrepancy is witnessed between the test data from the bioluminescence and fluorescence tests this may be an indication of experimental error and the need for further testing.

FIG. 1 shows a toxicity test system 200 comprising: an aqueous suspension 30 of dinoflagellates 10; a test chamber 300; an optical signal generator 40; a first optical transducer 46; a stimulator 20; a second optical transducer 26; and an analyzer 50. The test chamber 300 is capable of containing the aqueous suspension 30 of dinoflagellates 10, in which a test sample 60 may be immersed. For example, the test sample 60 may be soil, sediment, water, or any other substance with a toxicity that is desired to be ascertained. The optical signal generator 40 is capable of emitting an excitation signal 140 for exciting the dinoflagellates 10 to emit a fluorescence signal 145 if the dinoflagellates 10 are alive. The fluorescence signal 145 may be detected and transformed by the first optical transducer 46 into a fluorescence data signal 146. The stimulator 20 is capable of generating a pressure pulse for stimulating live dinoflagellates 10 to emit a bioluminescence signal 125. The bioluminescence signal 125 may be detected and transformed into a bioluminescence data signal 126 by the second optical transducer 26. The analyzer 50 is disposed to receive and transform the bioluminescence data signal 126 and the fluorescence data signal 146 into an output 150, which represents the toxicity of the test sample 60.

Figure 2:
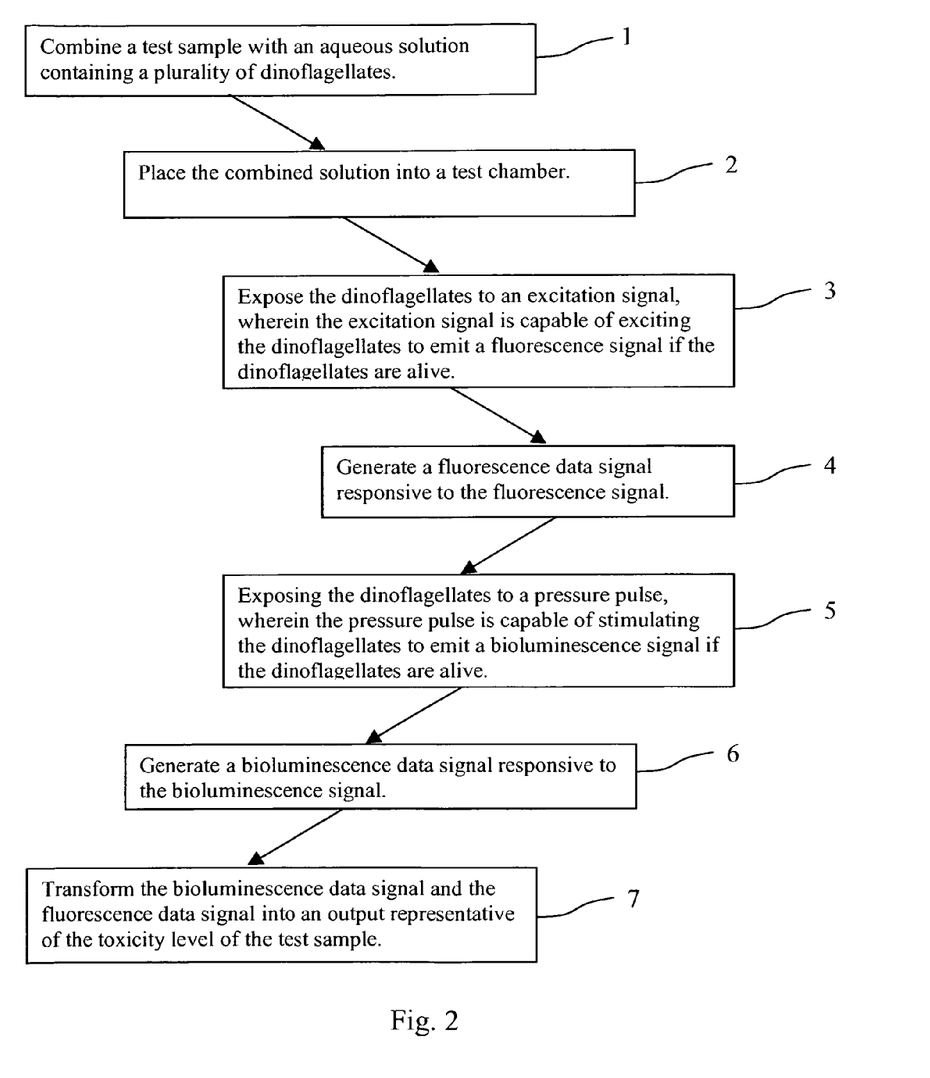
FIG. 2 shows a method of determining the toxicity of a test sample.

FIG. 2 illustrates a method of utilizing system 200 to determine the toxicity level of a test sample 60. In step 1, the test sample 60 may be combined with aqueous suspension 30 of dinoflagellates 10. The aqueous suspension 30 and the test sample 60 are placed into the test chamber 300 in step 2. It is to be understood that the test sample 60 may be combined with the aqueous suspension 30 before or after aqueous suspension 30 has been placed in the test chamber 300. In step 3, the dinoflagellates 10 may be exposed to an excitation signal 140, which is capable of exciting the dinoflagellates 10 that are alive to emit a fluorescence signal 145. In step 4, a fluorescence data signal 146 may be generated in response to the fluorescence signal 145. In step 5, the dinoflagellates 10 may be exposed to a pressure pulse, which is capable of stimulating the dinoflagellates 10 to emit a bioluminescence signal 125. In step 6, a bioluminescence data signal 126 may be generated in response to the bioluminescence signal 125. In step 7, the bioluminescence data signal 126 and the fluorescence data signal 146 may be transformed into an output, which is representative of the toxicity level of the test sample 60. Steps 5 and 6 may precede steps 3 and 4 and vice versa.

The dinoflagellates 10 in aqueous suspension 30 may be any species of dinoflagellates that fluoresce in response to a stimuli and bioluminesce in response to shear-stress inducing pressure pulses. Example embodiments of dinoflagellates 10 include, but are not limited to, *Gonyaulax polyedra, Pyrocystis lunula, Pyrocystis fusiformis,* and *Pyrodinium bahamense*. These species may be maintained, prior to testing, in enriched seawater medium according to American Society for Testing and Materials Standard Guide for Conducting Static 96-h Toxicity Tests with Microalgae (ASTM 1990). Any number of dinoflagellate cells 10 may be added to aqueous suspension 30 provided their bioluminescence and fluorescence responses are measurable. By way of example, the population density of dinoflagellates 10 may be in the range of about 1 to about 500 dinoflagellate cells per milliliter of aqueous suspension 30. For example, about 3 milliliters of aqueous suspension 30 may comprise about 600 dinoflagellates. In another example, about 3 milliliters of aqueous suspension 30 may comprise about 300 dinoflagellates.

Figure 3:
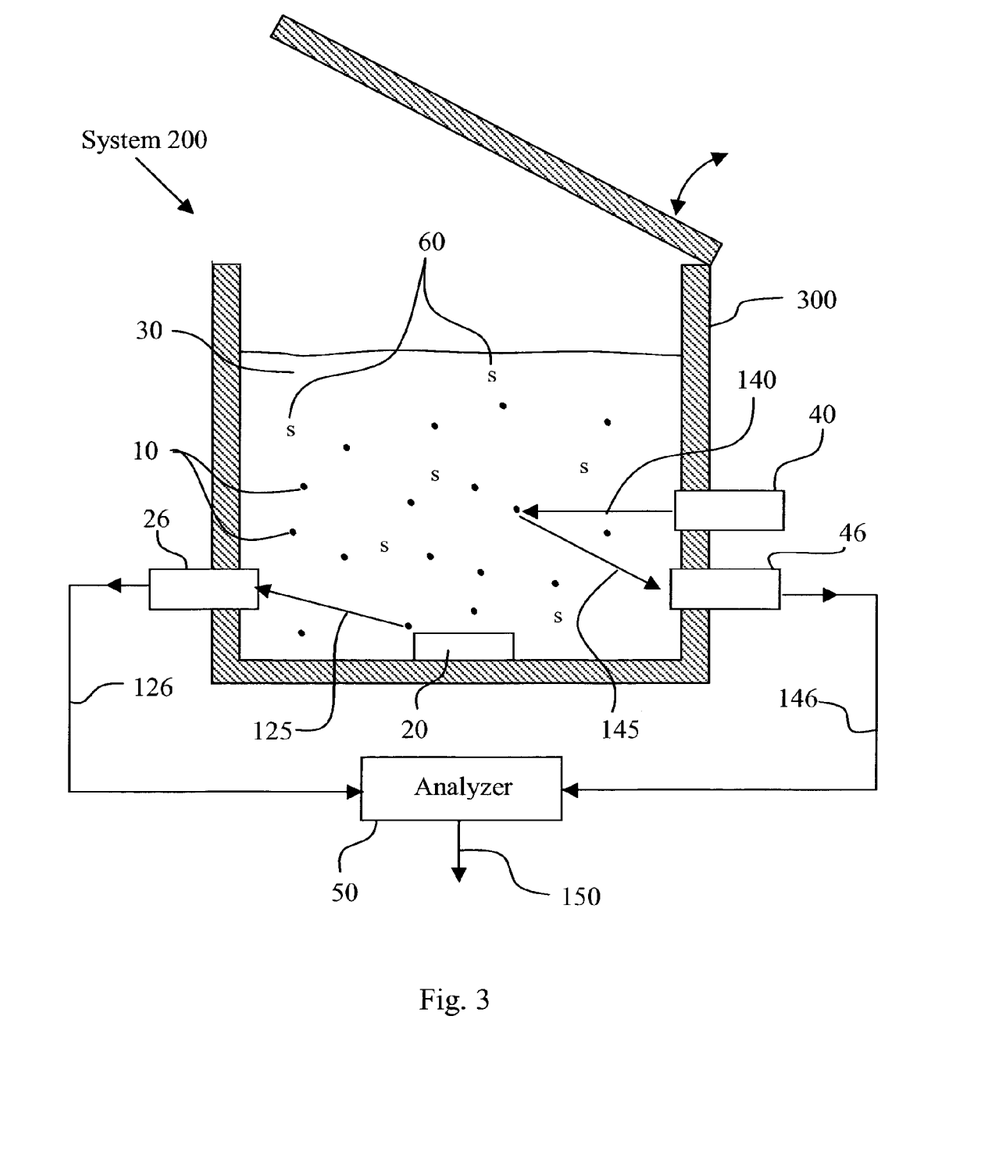
FIG. 3 shows an embodiment of a toxicity test system with an ambient light tight test chamber in an open configuration.
Figure 4:
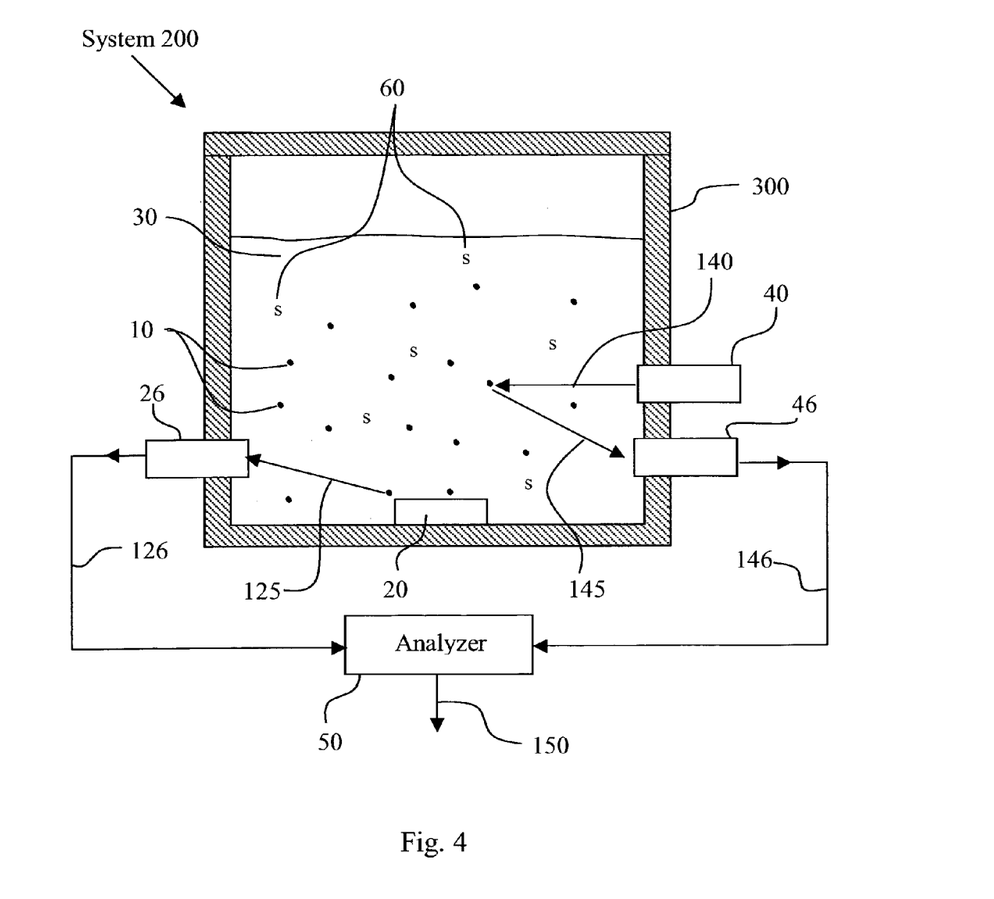
FIG. 4 shows an embodiment of a toxicity test system with an ambient light tight test chamber in a light-tight configuration.
Figure 5:
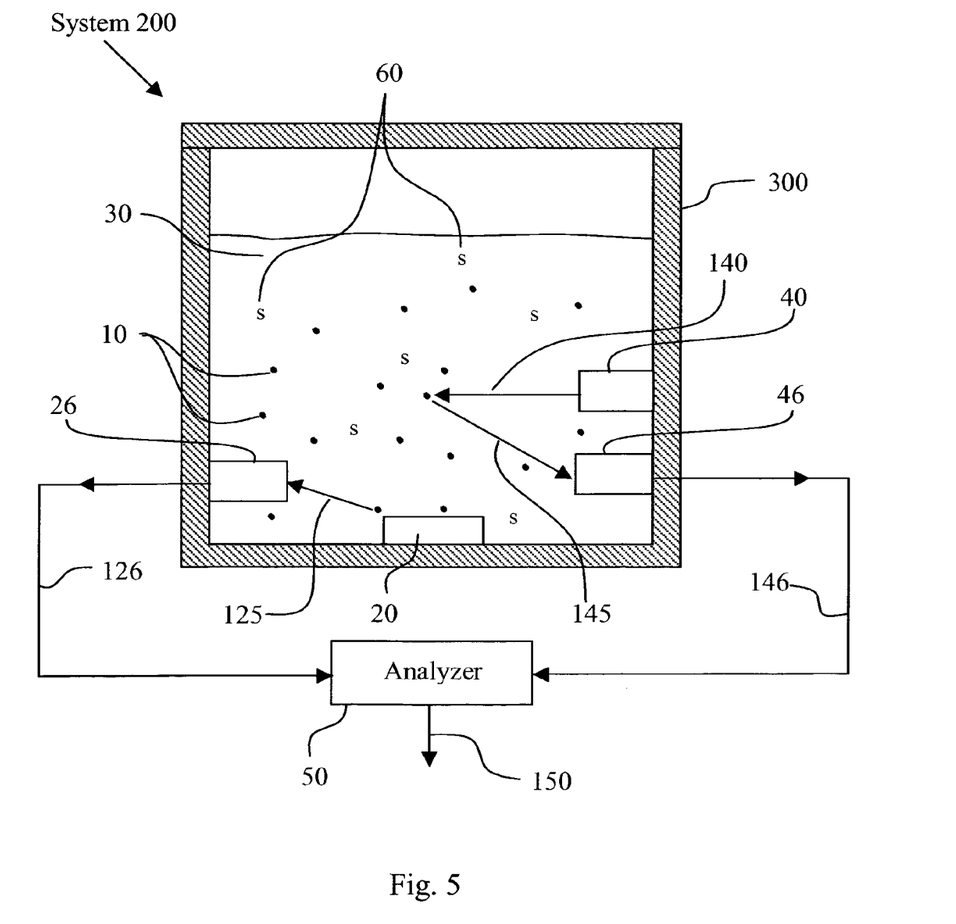
FIG. 5 shows an embodiment of a toxicity test system with system elements located inside the test chamber.

The test chamber 300 may be in an opened or light-tight configuration. In its opened configuration, as shown in FIG. 3, the test chamber 300 may allow for the insertion of aqueous suspension 30 and a test sample 60. In its light-tight configuration, as shown in FIG. 4, the test chamber 300 may be ambient light-tight such that most ambient light may not enter the test chamber 300. The optical signal generator 40, the first optical transducer 46, the stimulator 20, and the second optical transducer 26 may be operably coupled to the test chamber 300 to prevent ambient light from entering the test chamber 300. The optical signal generator 40 may be operably coupled to the test chamber such that the excitation signal 140 may excite dinoflagellates 10 in the test chamber 300 when the test chamber 300 is in its light-tight configuration, as shown in FIG. 4. FIG. 4 shows the optical signal generator 40 as being may be mounted partially inside and outside the test chamber 300. It is to be understood that any coupling arrangement of optical signal generator 40 to the test chamber 300 is suitable if that arrangement allows the excitation signal 140 to excite dinoflagellates 10 while dinoflagellates 10 are contained in test chamber 300. For example, FIG. 5 shows another embodiment of system 200 wherein the optical signal generator 40 may be operably coupled to the test chamber 300 from entirely inside the test chamber 300.

The optical signal generator 40 is capable of generating an excitation signal 140 for exciting the dinoflagellates 10 to emit a fluorescence signal 145. Example embodiments of the optical signal generator 40 include, but are not limited to, a laser, a light emitting diode (LED), and any other optical signal generator capable of stimulating dinoflagellates 10 to emit fluorescence signal 145. The excitation signal 140 may be any signal capable of exciting the dinoflagellates 10 to emit a fluorescence signal 145. In one embodiment, the excitation signal may be a continuous, blue, optical signal with a wavelength in the range of about 420 to about 440 nanometers. The fluorescence signal 145 may be any signal generated by the dinoflagellates 10 in response to being excited by the excitation signal 140. For example, in one embodiment, the optical signal generator 40 may be an LED, which is capable of generating an excitation signal 140 having a wavelength of about 430 nanometers, which may then propagate into the test chamber 300 exciting dinoflagellates 10 to emit a fluorescence signal 145 having a wavelength of about 663 nanometers.

The first optical transducer 46 may be operably coupled to the test chamber 300 such that the first optical transducer 46 is capable of detecting the fluorescence signal 145 from excited dinoflagellates 10 in the test chamber 300, as shown in FIG. 4. In response to detecting the fluorescence signal 145, the first optical transducer 46 may then generate the fluorescence data signal 146, an electrical signal, which is representative of a characteristic of interest of the fluorescence signal 145. Characteristics of interest of the fluorescence signal 145 include, but are not limited to, intensity, duration, wavelength, and photon count. For example, if the fluorescence signal 145 has an intensity x the fluorescence data signal 146 will have a unique value that is representative of the intensity x. FIG. 4 shows the first optical transducer 46 as being mounted partially inside and outside the test chamber 300. However, it is to be understood that any coupling arrangement of the first optical transducer 46 to the test chamber 300 is suitable if that arrangement allows the first optical transducer 46 to detect the fluorescence signal 145 from excited dinoflagellates 10 in the test chamber 300. For example, FIG. 5 shows an embodiment of system 200 wherein the first optical transducer 46 may be mounted entirely inside the test chamber 300. The first optical transducer 46 may be any device capable of generating the fluorescence data signal 146 in response to the fluorescence signal 145. Example embodiments of the first optical transducer 46 include, but are not limited to, a photomultiplier tube, a photodiode, a charge-coupled device (CCD), and any other device capable of generating a fluorescence data signal 146 in response to detecting the fluorescence signal 145.

The stimulator 20 may be operably coupled to the test chamber 300 such that the stimulator 20 is capable of stimulating the dinoflagellates 10 in the test chamber 300 to emit bioluminescence signal 125. The stimulator 20 may be any device capable of stimulating the dinoflagellates 10 to emit bioluminescent signal 125 by introducing pressure pulses into aqueous suspension 30. Example embodiments of the stimulator 20 include, but are not limited to, an ultrasonic pulse generator, a shaking device, a stirring device, an acoustic transducer (as disclosed in U.S. Pat. No. 5,840,572 to Copeland), and any other device capable of stimulating live dinoflagellates 10 to bioluminesce. For example, one embodiment of the stimulator 20 may include a motor-driven propeller 26, which may stir the aqueous suspension 30 and the test sample 60, thereby generating pressure pulses which tend to simulate the dinoflagellates 10 to emit bioluminescent signal 125. The wavelength of the bioluminescence signal 125 will generally lie within the range of about 450 to about 500 nanometers.

The second optical transducer 26 is operably coupled to the test chamber 300 such that the second optical transducer 26 is capable of detecting the bioluminescence signal 125 from excited dinoflagellates 10 in the test chamber 300, as shown in FIG. 4. In response to detecting the bioluminescence signal 125, the second optical transducer 26 may then generate the bioluminescence data signal 126, an electrical signal, which is representative of a characteristic of interest of the bioluminescence signal 125. Characteristics of interest of the bioluminescence signal 125 include, but are not limited to, intensity, duration, wavelength, and photon count. FIG. 4 shows the second optical transducer 26 as being mounted partially inside and outside the test chamber 300. However, it is to be understood that any coupling arrangement of the second optical transducer 26 to the test chamber 300 is suitable if that arrangement allows the second optical transducer 26 to detect the bioluminescence signal 125 from excited dinoflagellates 10 in the test chamber 300 when the test chamber 300 is in its light-tight configuration. For example, FIG. 5 shows an embodiment of system 200 wherein the second optical transducer 26 may be mounted entirely inside the test chamber 300. The second optical transducer 26 may be any device capable of generating the bioluminescence data signal 126 in response to the bioluminescence signal 125. Example embodiments of the second optical transducer 26 include, but are not limited to, a photomultiplier tube, a photodiode, a CCD, and any other device capable of generating a bioluminescence data signal 126 in response to detecting the bioluminescence signal 125.

Figure 9:
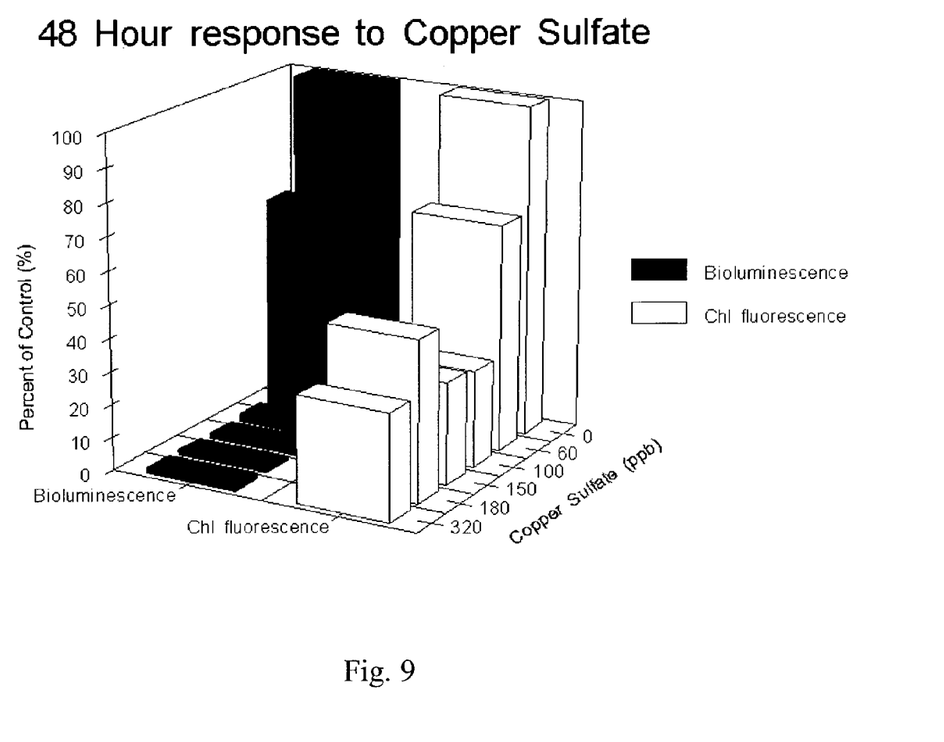
FIG. 9 shows the correlation of the bioluminescence response and the fluorescence response of dinoflagellates exposed to varying amounts of a toxin.

The analyzer 50 may be any device capable of receiving and transforming the bioluminescence data signal 126 and the fluorescence data signal 146 into an output 150, which represents the toxicity of the test sample 60. Transforming the bioluminescence data signal 126 and the fluorescence data signal 146 into an output 150 may be accomplished by measuring the fluorescence data signal 146 and the bioluminescence data signal 126 against a control or a known fluorescence and bioluminescence standard. Mean relative fluorescence, standard deviation, and the coefficient of variation may be calculated by the analyzer 50 for the aqueous suspension 30 of dinoflagellates 10 in the test chamber 300. Relative fluorescence, calculated as a percentage of control values, can be plotted over time during the test. Example embodiments of the analyzer 50 include, but are not limited to, a processor, a gauge, and a any other device capable of correlating the bioluminescence data signal 126 and the fluorescence data signal 146 and generating an output 150 that represents the toxicity of the test sample 60. The output 150 may be any audio, visual, or tactile output capable of communicating to a user the toxicity level of the test sample 60. Although FIG. 1 shows the output 150 as exiting the analyzer 50, it is to be understood that the output 150 may also be used as an input to an internal function of the analyzer, or used as an input to another device or system. The Analyzer may also control the sequence of testing. For example, after the aqueous suspension 30 has been placed in the test chamber 300 and the test chamber 300 is in its ambient light-tight configuration, the analyzer 50 may turn on the optical signal generator 40 to emit the excitation signal 140 for y seconds (where y is an integer). During the emission of excitation signal 140 the analyzer 50 may record the fluorescence data signal 146 generated by the first optical transducer 46 in response to detecting fluorescence signal 145. After y seconds, the stimulator 20 may be activated by the analyzer 50 to stimulated the dinoflagellates 10 to emit a bioluminescence signal 125. When the optical signal generator 40 is not emitting the excitation signal 140 and the stimulator has introduced pressure pulses into the aqueous suspension 30, the analyzer 50 may record the bioluminescence data signal 126 generated by the second optical transducer 26 in response to detecting the bioluminescence signal 125 emitted by stimulated dinoflagellates 10. FIG. 9 is a graph showing the functional relationship between the fluorescence data signal 146, the bioluminescence data signal 126, and the toxicity of the test sample 60. The data from the fluorescence data signal 146 and the bioluminescence data signal 126 may be compared to previous test results or to data stored in a look-up-table stored in the analyzer 50.

Figure 6:
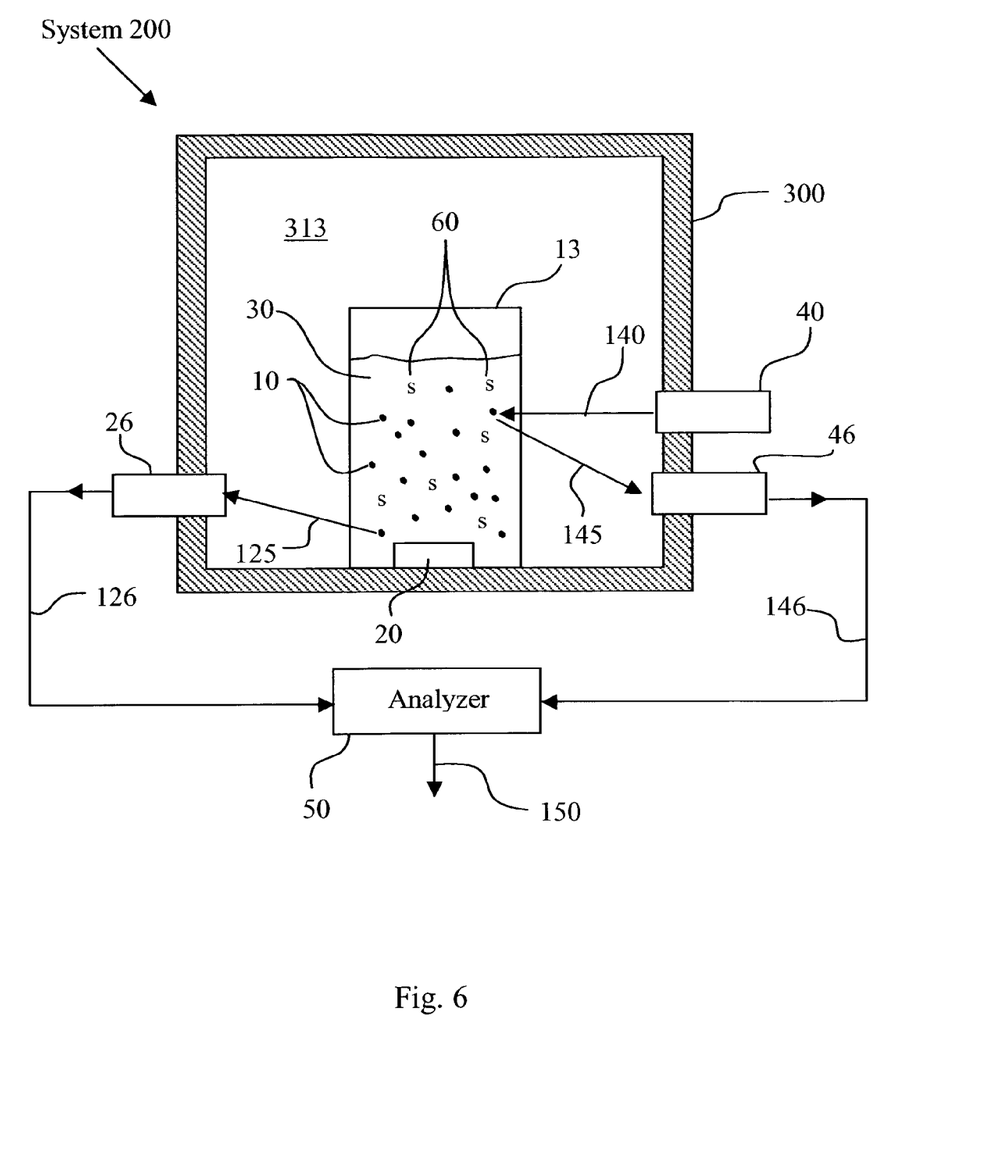
FIG. 6 shows an embodiment of a toxicity test system with a removable sample container.

FIG. 6 illustrates another embodiment of system 200 where the aqueous suspension 30 and the test sample 60 may be contained in a removable sample container 13. The sample container 13 is capable of being inserted into a cavity 313 of the test chamber 300 when the test chamber 300 is in the opened configuration. The cavity 313 serves to support the sample container 13 when the test chamber 300 is in the light-tight or opened configuration. By way of example, the sample container may be a test tube, a cuvette, or any other container capable of fitting inside the test chamber 300 and containing aqueous suspension 30. The sample container 13 may be made of polystyrene, glass, polycarbonate, or any other material that is optically transparent to the wavelengths of the excitation signal 140, the fluorescence signal 145, and the bioluminescence signal 125. The sample container 13 may be made of a material which is chemically non-reactive with sea water, as for example, glass, DELRIN®, polycarbonate, or polystyrene. The size and shape of the sample container 13 are limited only by the size and shape of the cavity 313. The size and shape of the cavity 313 may be any size and shape that allows for the uninhibited transmission of the excitation signal 140, the fluorescence signal 145 and the bioluminescence signal 125 through cavity 313. In another embodiment, the cavity 313 may support multiple sample containers 13 simultaneously.

Figure 7:
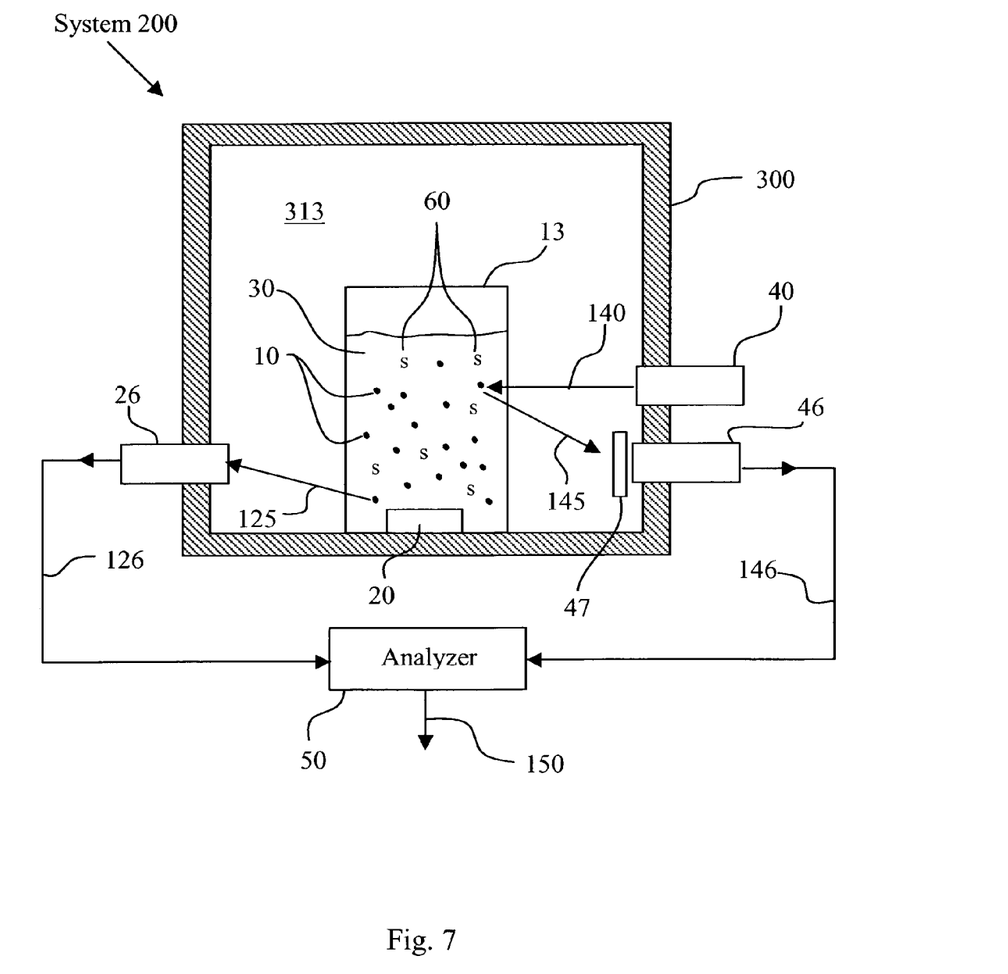
FIG. 7 shows an embodiment of a toxicity test system including an optical filter.

FIG. 7 illustrates another embodiment of system 200 further comprising a red optical filter 47 optically coupled between the dinoflagellates 10 and the first optical transducer 46. The red optical filter 47 may be any optical filter capable of preventing the excitation signal 140 from being detected by the first optical transducer 46 while allowing the fluorescence signal 145 to be transmitted through the red optical filter 47 to the first optical transducer 46. For example, the red optical filter 47 may be a wavelength-selective filter that only allows passage of optical signals falling within the range of about 660-690 nanometers.

Figure 8:
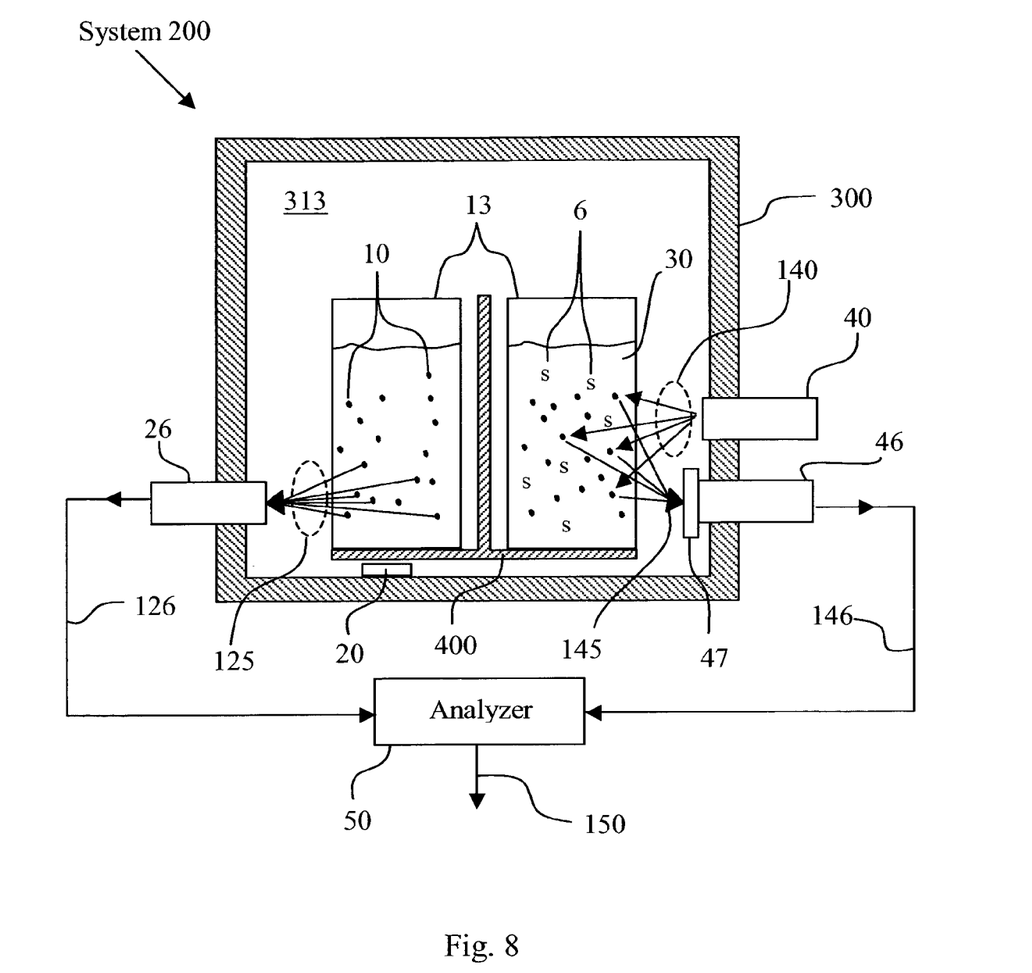
FIG. 8 shows an embodiment of a toxicity test system comprising multiple sample containers and an optical isolator.

FIG. 8 illustrates another embodiment of system 200 further comprising at least two sample containers 13 housed in the test chamber 300 and optically isolated from each other by an optical isolator 400. The optical isolator 400 prevents any optical signals emanating from one sample container 13 from interfering with the optical signals emanating from another sample container 13. The optical isolator 400 may be operatively coupled to a stepper motor to rotate the sample containers 13 within the test chamber 300 thus allowing the dinoflagellates 10 in each sample container 13 to be tested for fluorescence and bioluminescence inhibition without interference from optical signals emanating from other sample containers 13. Various amounts of test sample 60 may be added to each of the sample containers 13 to improve statistical significance.

From the above description of the system and method for quantifying toxicity in water, soils and sediments, it is manifest that various techniques may be used for implementing the concepts of system 200 without departing from its scope. The described embodiments are to be considered in all respects as illustrative and not restrictive. It should also be understood that system 200 is not limited to the particular embodiments described herein, but is capable of many embodiments without departing from the scope of the claims.

We claim:
1. A toxicity test system comprising:
an aqueous suspension of dinoflagellates;
a test chamber capable of containing said aqueous suspension of dinoflagellates and a test sample;
an optical signal generator capable of emitting an excitation signal, said excitation signal capable of exciting said dinoflagellates to emit a fluorescence signal if said dinoflagellates are alive;
a first optical transducer capable of producing a first data signal in response to detecting said fluorescence signal;
a stimulator capable of generating a pressure pulse, wherein said pressure pulse is capable of stimulating said dinoflagellates to emit a bioluminescence signal if said dinoflagellates are alive;
a second optical transducer capable of producing a second data signal in response to detecting said bioluminescence signal; and
an analyzer disposed to compare said first data signal and said second data signal to a control data to generate an output representing the toxicity of said test sample.

2. The system of claim 1, wherein said test chamber is ambient-light-tight.

3. The system of claim 1, wherein said dinoflagellates are *Gonyaulax polyedra*.

4. The system of claim 1, wherein said dinoflagellates are *Pyrocystis lunula*.

5. The system of claim 1, wherein said first optical transducer is a photodiode.

6. The system of claim 5, further comprising a red optical filter optically coupled between said dinoflagellates and said first optical transducer, the red optical filter disposed to filter said fluorescence signal.

7. The system of claim 1, wherein said second optical transducer is a photodiode.

8. The system of claim 1, wherein the wavelength of said excitation signal is about 430 nanometers.

9. The system of claim 1, wherein said stimulator is a motor-driven propeller.

10. The system of claim 1, wherein said aqueous suspension comprises about 100 to about 600 dinoflagellates.

11. The system of claim 1, wherein said second optical transducer is a photomultiplier tube.

12. The system of claim 2, further comprising at least two transparent sample containers capable of containing said aqueous suspension and said test sample, said sample containers capable of being simultaneously supported inside said test chamber, wherein each of said sample containers is optically isolated from each other of said sample containers.

13. A toxicity testing method comprising:
   combining a test sample with a first aqueous suspension containing a first plurality of dinoflagellates;
   placing said combined suspension into a test chamber;
   exposing said dinoflagellates to an excitation signal, wherein said excitation signal is capable of exciting said dinoflagellates to emit a fluorescence signal if said dinoflagellates are alive;
   generating a first data signal in response to detecting said fluorescence signal;
   exposing said dinoflagellates to a pressure pulse, wherein said pressure pulse is capable of stimulating said dinoflagellates to emit a bioluminescence signal if said dinoflagellates are alive;
   generating a second data signal in response to detecting said bioluminescence signal; and
   transforming said second data signal and said first data signal into an output representative of the toxicity level of said test sample by comparing said second data signal and said first data signal to a control data.

14. The method of claim 13, wherein said control data comprises control-f data and control-b data obtained by performing the following steps:
   placing a second aqueous suspension containing a second plurality of dinoflagellates into said test chamber;
   exposing said second dinoflagellates to said excitation signal, wherein said excitation signal is capable of exciting said second dinoflagellates to emit a first control signal;
   generating a control-f data signal in response to detecting said first control signal;
   storing said control-f data signal as control-f data;
   exposing said second dinoflagellates to a pressure pulse, wherein said pressure pulse is capable of stimulating said second dinoflagellates to emit a second control signal;
   generating a control-b data signal in response to detecting said second control signal;
   storing said control-b data signal as control-b data.

15. The method of claim 14, wherein said test chamber is ambient-light-tight.

16. The method of claim 15, wherein said second and first dinoflagellates are from the same cultivated stock of dinoflagellates.

17. The method of claim 15, wherein said test sample is soil.

18. The method of claim 15, wherein said test sample is sediment.

19. The method of claim 15, wherein said test sample is water.

* * * * *